(12) United States Patent
Zhang et al.

(10) Patent No.: US 10,487,304 B1
(45) Date of Patent: Nov. 26, 2019

(54) CHEMICALLY ASSISTED RAPID ALGAE HARVESTING FROM DILUTE PHASE

(71) Applicants: Chen Zhang, Huntsville, AL (US); James E. Smith, Jr., Huntsville, AL (US)

(72) Inventors: Chen Zhang, Huntsville, AL (US); James E. Smith, Jr., Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 15/397,499

(22) Filed: Jan. 3, 2017

Related U.S. Application Data

(63) Continuation-in-part of application No. 14/975,139, filed on Dec. 18, 2015, now Pat. No. 9,994,791.

(60) Provisional application No. 62/273,582, filed on Dec. 31, 2015.

(51) Int. Cl.
  *C12N 5/00* (2006.01)
  *C12N 1/12* (2006.01)
  *C12N 1/06* (2006.01)

(52) U.S. Cl.
  CPC .................................. *C12N 1/12* (2013.01); *C12N 1/06* (2013.01)

(58) Field of Classification Search
  CPC .................................. C12N 1/12; C12N 1/06
  USPC ....................................................... 435/410
  See application file for complete search history.

(56) References Cited

U.S. PATENT DOCUMENTS

| | | |
|---|---|---|
| 5,539,133 A | 7/1996 | Kohn et al. |
| 8,148,559 B1 | 4/2012 | Walker et al. |
| 8,329,449 B2 | 12/2012 | Poenie et al. |
| 8,772,004 B2 | 7/2014 | Schafron et al. |
| 8,859,270 B2 | 10/2014 | Echevarria Parres |
| 9,085,745 B2 | 7/2015 | Eckelberry et al. |
| 9,994,791 B1 | 6/2018 | Zhang et al. |
| 2011/0086386 A1* | 4/2011 | Czartoski ................. C12N 1/06 435/67 |

(Continued)

FOREIGN PATENT DOCUMENTS

CN    103045352    4/2013

OTHER PUBLICATIONS

Wikipedia, Citric acid, Nov. 2014, p. 1-8. (Year: 2014).*

(Continued)

*Primary Examiner* — Taylor V Oh
(74) *Attorney, Agent, or Firm* — Maynard Cooper & Gale, P.C.; Jon E. Holland

(57) ABSTRACT

The present disclosure generally pertains to methods for the harvesting of biomass, in particular algae, from dilute aqueous suspension. In one embodiment, the method comprises the steps of: adjusting the pH of the dilute aqueous suspension to cause disruption of the algal cell walls and exposure of the hydrophobic tails of the algal lipid bilayer; adding at least one organic solvent to the dilute aqueous suspension; and mixing the dilute aqueous suspension. The method may also include the steps of: waiting for formation of an organic layer from the dilute aqueous suspension; and recovering the organic layer. The organic layer rises to the top of the dilute aqueous suspension, allowing for mechanical separation or decanting of the organic layer.

11 Claims, 1 Drawing Sheet

(56) References Cited

U.S. PATENT DOCUMENTS

2012/0228224 A1    9/2012  Kale

OTHER PUBLICATIONS

Zhang, et al., U.S. Appl. No. 14/975,139, entitled, "Method for Lipids from Algae," filed Dec. 18, 2015.
Coward, et al., "Harvesting microalgae by CTAB-aided foam flotation increases lipid recovery and improves fatty acid methyl ester characteristics," Biomass and Bioenergy, 2014, 67, p. 354-362.

* cited by examiner

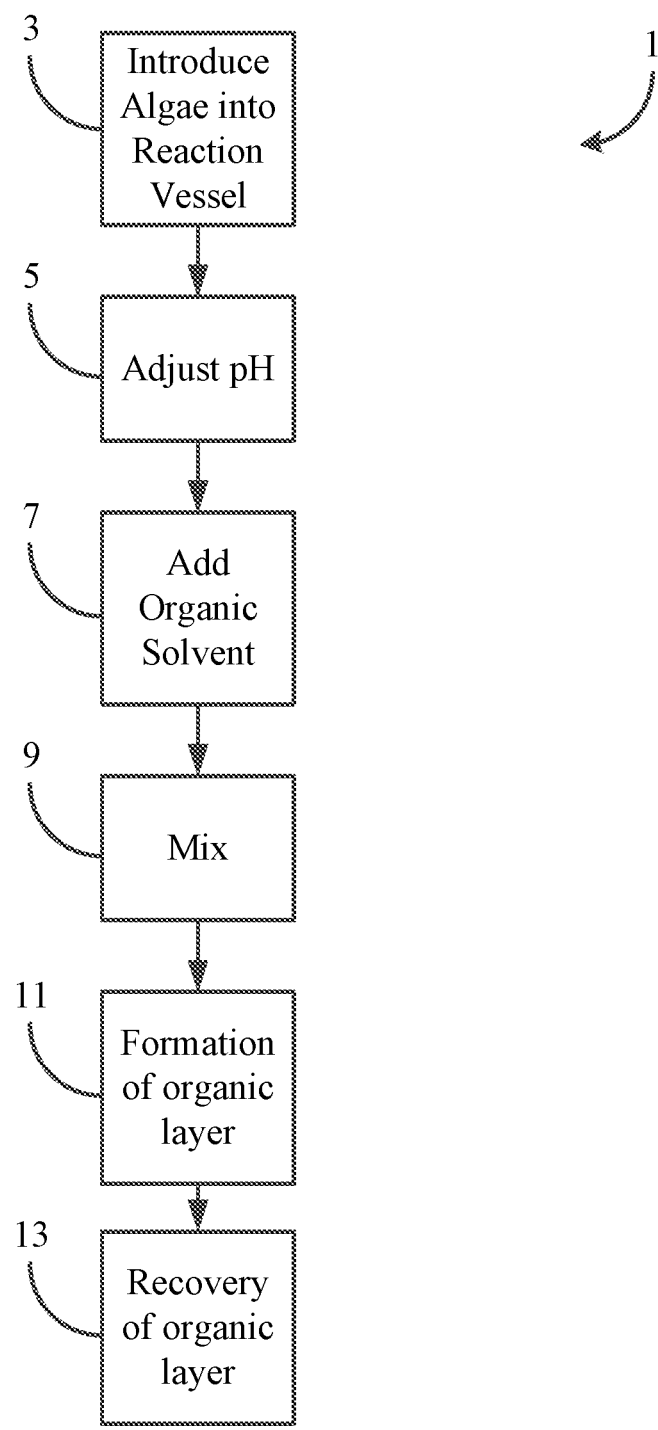

CHEMICALLY ASSISTED RAPID ALGAE HARVESTING FROM DILUTE PHASE

CROSS REFERENCE TO RELATED APPLICATION

This application is a continuation-in-part of U.S. patent application Ser. No. 14/975,139, entitled "Method for Extracting Lipid from Algae" and filed on Dec. 18, 2015, which is incorporated herein by reference. This application also claims priority to U.S. Provisional Patent Application No. 62/273,582, entitled "Chemically Assisted Rapid Algae Harvesting" and filed on Dec. 31, 2015, which is incorporated herein by reference.

RELATED ART

Conventional gasoline and diesel fuels are subject to considerable price fluctuations and have a limited supply. Machines that operate on gasoline and diesel fuel, however, may use biofuels as an alternative source of energy. Algae, in particular, possess the ability to convert sunlight into lipids that may be processed into biofuels and have the potential to produce up to sixty times more lipids per acre than land-based plants.

The commercial algal biofuel downstream processes—such as algal culture harvesting, drying, extraction, and algal lipid transesterification—are not yet economically feasible. One of the major bottlenecks to such economic feasibility is developing cost-efficient and energy-efficient methods of algae harvesting and drying. Algae are suspended in a dispersed state in dilute cultures and have extremely small size with cell density similar to that of the surrounding growth media. To process algae into biofuel usually requires separating the algae from its growth media, which is difficult and costly as a result of such a dilute suspension. As a result, it has been suggested in the literature that up to 30% of the total cost algal biodiesel production is related to biomass harvesting.

Currently, economically feasible algae harvesting methods remain elusive. The cultivation of microalgae typically results in algal biomass in dilute suspension with concentrations of 0.1-2 g/L of dry algae, depending on the cultivation system used, which means a typical algae culture only contains 0.01-0.2% dry mass. Therefore, many conventional harvesting methods are not economically feasible due to large quantity of water needed for separation and concentration. Centrifugation is an effective method that is widely used, but it leads to extremely high capital and operational cost. Flocculation is another popular method, but the required chemicals, flocculants, may be too expensive to be commercially viable, the yield of recovered algal biomass is relatively low, and the sedimentation rate is slow.

SUMMARY OF INVENTION

In some embodiments, the present disclosure pertains to a method for harvesting algae from a dilute aqueous suspension, comprising the steps of: adjusting the pH of the dilute aqueous suspension to cause disruption of the algal cell walls and exposure of the hydrophobic tails of the algal lipid bilayer; adding at least one organic solvent to the dilute aqueous suspension; and mixing the dilute aqueous suspension. In some embodiments, the at least one organic solvent is partially water soluble. In some embodiments, the at least one organic solvent comprises ethyl acetate. In some embodiments, the pH is adjusted using carbon dioxide. In other embodiments, the pH is adjusted using citric acid. In some embodiments, the algae is *Nannochloropsis salina*, and the pH is adjusted from about pH 7 to about pH 4.5 using citric acid. In some embodiments, the method is performed at a temperature between about 0° C. and 100° C. In some embodiments, the temperature is about room temperature.

In some embodiments, the method further comprises the steps of: waiting for formation of an organic layer from the dilute aqueous suspension; and recovering the organic layer. In some embodiments, the duration of the waiting is less than one minute. In some embodiments, the organic layer is recovered by decanting the organic layer from the dilute aqueous suspension. In some embodiments, the organic layer is recovered by mechanical separation of the organic layer from the dilute aqueous suspension.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 1 is a flow chart of an exemplary method for harvesting algae from a dilute aqueous suspension.

DETAILED DESCRIPTION

The present disclosure generally pertains to methods for the harvesting of biomass, in particular algae, from dilute aqueous suspension. In one embodiment, the method comprises the steps of: adjusting the pH of the dilute aqueous suspension to cause disruption of the algal cell walls and exposure of the hydrophobic tails of the algal lipid bilayer; adding at least one organic solvent to the dilute aqueous suspension; and mixing the dilute aqueous suspension. The method may also include the steps of: waiting for formation of an organic layer from the dilute aqueous suspension; and recovering the organic layer. The organic layer rises to the top of the dilute aqueous suspension, allowing for mechanical separation or decanting of the organic layer.

As used herein, the term "about" means plus or minus approximately ten percent of a numerical value, such that "about 20° C." indicates a temperature between approximately 18° C. and 22° C.

As used herein, the term "algae" includes, but is not limited to, microalgae. Some non-limiting examples of algae include *Nannochloropsis salina, Dunaliella salina*, and other algae suitable for lipid extraction known in the art.

As used herein, the term "dilute aqueous suspension" means an aqueous suspension that contains less than about 50% of dry algal biomass by weight. A dilute aqueous suspension may include, but is not limited to, a suitable culture medium in which algae is grown.

As used herein, the term "partially water soluble" means between about 0.00001% and about 80% by volume soluble in water.

FIG. 1 depicts an exemplary flow chart of a method 1 of harvesting algae from a dilute aqueous suspension. In one embodiment, the harvesting process 1 is performed at temperatures between 0° C. to 100° C. In an additional embodiment, the harvesting process 1 is performed at room temperature, i.e., between about 20° C. to 26° C. The extraction process 1 may be performed at other temperature ranges in other embodiments.

Referring again to FIG. 1, as indicated by box 3, a dilute aqueous suspension of algae is obtained from any source commonly known in the art. The dilute aqueous suspension containing algal cells can be concentrated or diluted, but typically is used as grown in the environment, i.e., without isolation or concentration of the algae cells. The dilute aqueous suspension may be a dilute aqueous suspension. In this embodiment of the disclosure, it is not necessary to centrifuge, dry or dewet the algae culture. This is an advantage of the present disclosure compared to conventional algae harvesting, which includes a centrifugation and/or dewetting process that requires significant energy input and is highly energy intensive. Eliminating the need for centrifugation and a dewetting step, as disclosed herein, significantly reduces the costs of the presently described harvesting method 1. Further, in certain embodiments, the dilute aqueous suspension may contain a mixture of, i.e., more than one, algae strains.

Referring again to FIG. 1, the pH level of the dilute aqueous suspension is then modified to optimize algae harvesting, as indicated in box 5; the change in pH level disrupts the algal cell walls and causes the hydrophobic tails of the lipid bilayer to be exposed. The pH level may be increased or decreased from the pH present in a typical algal growing environment. The optimal pH level for algae harvesting is dependent upon the strain of the algae in use. The pH modifying agent may comprise a chemical, a combination of chemicals, a gas, or a combination of gases. Such pH modifying agents include, but are not limited to, citric acid, hydrobromic acid, hydrochloric acid, hydroiodic acid, nitric acid, perchloric acid, phosphoric acid, and sulfuric acid. In one embodiment, the pH level of the culture is lowered by the addition of an acid, for instance citric acid. In this embodiment, the lower pH weakens the algae cell walls by affecting the tertiary structure of the proteins (intrinsic and extrinsic) held within the bi-layer of the phospholipid membrane, allowing extraction of the algal intracellular contents. In one example, lowering the acidity of *Nannochloropsis salina* culture from its natural level of pH 7 to about pH 4.5 causes disruption of the algae cell walls sufficient for algae harvesting by the currently described method 1.

Lipids isolated from algae are generally soluble in organic solvents but insoluble in water. As a result, the lipid matter of the algal cell may still be contained within the disrupted cell wall after pH adjustment (box 5), because it is surrounded by water within the dilute aqueous suspension. The algal lipids present in the dilute aqueous suspension are not soluble in water and are difficult to extract from the algae debris. The process disclosed herein may be described as a liquid-liquid extraction. In such a liquid-liquid extraction, the solute of interest partitions between two immiscible phases. Generally, one phase is aqueous and the other phase is an organic solvent. Because the phases are immiscible they form two layers, with the denser phase on the bottom. The solute is initially present in one of the two phases as the immiscible nature of the two solvents acts to separate and select the compounds to be isolated. The process of extraction uses the solubility differences of the different substances in the suspension to selectively draw the desired product into one of the layers. Harvesting methods differ depending upon the density of the solvent being used. Harvesting efficiency, i.e., the percentage of solute moving from one phase to the other phase, is determined by the equilibrium constant for the solute's partitioning between the phases and any other reactions involving the solute. Here, the desired compounds, for example algal lipids, are pulled from a first phase into a second phase where the phases are not miscible. The harvesting process results in the formation of an organic layer.

Referring again to FIG. 1, at least one organic solvent is added to the dilute aqueous suspension, as indicated in box 7. The at least one organic solvent comprises at least one partially water soluble organic solvent. The use of partially water soluble organic solvents allows the algal lipids to spread out more evenly within the dilute aqueous suspension compared to the use of non-partially water soluble organic solvents. The organic solvent to water ratio depends on the concentration of algae in water. For an aqueous suspension with dry algae concentration of about 1.6 g/L, a preferred ratio used may be about 3:10 (volume:volume), but other ratios are possible in other embodiments. In one embodiment, the at least one organic solvent comprises ethyl acetate, an organic compound with the formula $C_4H_8O_2$. Ethyl acetate is the ester of ethanol and acetic acid and is fairly volatile at room temperature, having a boiling point of 77° C. Due to these properties, it can be removed from a sample by heating, for example in a hot water bath, and providing ventilation with compressed air. Other advantages of ethyl acetate include its low cost, its ability to rapidly decompose, and its low toxicity.

Referring again to FIG. 1, after adjustment of the pH (box 5) and addition of organic solvent (box 7), the dilute aqueous suspension is mixed (box 9). Thorough mixing is desirable to allow the algal lipids to be extracted into a single organic layer. In other embodiments, mixing of the organic solvent with the dilute aqueous suspension can be before or during the pH adjustment.

Referring again to FIG. 1, after mixing, the aqueous layer and the organic layer naturally separate from one another, as indicated by box 11. The organic layer rises to the top of the aqueous layer with no further assistance as a result of the algal cell wall disruption and exposure of the hydrophobic tail. This separation and migration process may occur in less than 1 minute for a dilute aqueous suspension with a dry algae concentration of about 1.6 g/L, although other durations are possible in other embodiments. If the at least one organic solvent comprises ethyl acetate, the organic layer will contain algae and approximately 3.3% of water at 20° C.

Referring again to FIG. 1, the organic layer containing the algal lipids is then recovered, as illustrated in box 13. The organic layer may be recovered from the aqueous layer by decanting the organic layer or by mechanical separation techniques known in the art, which allows for recovery of approximately 60-80% of the organic layer, depending on the ratio of organic solvent to aqueous phase used. Depending on the species of algae and decanting method, inclusion of the organic layer/water layer interface and the top of the water layer may be necessary to improve harvesting efficiency, because some combinations have the tendency to gather algae at the interface of the layers. The organic layer may be briefly mixed, for example for about five seconds, to cause the algal biomass to coagulate.

The organic layer containing the isolated algal lipids may then be directly processed Alternatively, the organic solvent, (e.g., ethyl acetate) may be removed from the organic layer (not shown) prior to processing. In the embodiment where the solvent comprises ethyl acetate, the removal process may be accomplished, for instance, through evaporation; use of a vacuum can yield approximately 95% recovery of ethyl acetate. In one embodiment, the harvesting method 1 may be repeated a plurality of times to improve yield. A typical algal lipid yield after one cycle of the harvesting method 1 is approximately 95%-98% of the total lipid content for the algae *Nannochloropsis salina*.

In an additional embodiment, the harvesting process 1 may be performed in a conventional laboratory setting, for instance using a separation funnel. In an additional embodiment, larger scale harvesting of algae may involve extraction using a mixer/settler system or other suitable equipment known in the art.

Any remaining aqueous layer may be discarded, because it has low concentration of ethyl acetate (approximately 8% according to ethyl acetate/water solubility data, not shown), which is easily biodegradable and has little risk of toxicity. In an alternate embodiment, the remaining aqueous layer may be treated to recycle ethyl acetate, for example by evaporation. In another embodiment, the aqueous layer may be neutralized to reach a pH of a typical algae culture, diluted, and then reused for cultivation. Ethyl acetate can be used by microalgae as carbon source, as long as the concentration of ethyl acetate or the organic solvent used is below the toxicity point for the specific species of algae.

Although the present disclosure may discuss a specific order of method steps, the order of the steps may differ from what is disclosed. Also, two or more steps may be performed concurrently or with partial concurrence. All such variations are within the scope of the application.

One advantage of the methodologies described herein is that energy input is only required for the mixing of the dilute aqueous suspension. No centrifugation or dewetting is required, thereby saving considerable time and energy compared with conventional harvesting processes. Further, the chemicals involved in the disclosed methodologies are low cost, may be recovered after use, and are environmentally friendly with low risk of toxicity. In addition, the process requires fewer steps compared to conventional harvesting methods and may be completed in less time.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

Now, therefore, the following is claimed:

1. A method for harvesting algae from a dilute aqueous suspension, comprising the steps of:
   adjusting the pH of the dilute aqueous suspension sufficient to cause disruption of the algal cell walls and exposure of the hydrophobic tails of the algal lipid bilayer, wherein the concentration of algae in the dilute aqueous solution is between 0.1 and 2 q/L;
   adding at least one organic solvent to the dilute aqueous suspension, wherein the at least one organic solvent comprises a partially water soluble organic solvent; and
   mixing the dilute aqueous suspension.

2. The method of claim 1, wherein the at least one organic solvent comprises ethyl acetate.

3. The method of claim 1, wherein the pH is adjusted using carbon dioxide.

4. The method of claim 1, wherein the pH is adjusted using citric acid.

5. The method of claim 1, wherein the algae is *Nannochloropsis salina*, and the pH is adjusted from about pH 7 to about pH 4.5 using citric acid.

6. The method of claim 1, wherein the method is performed at a temperature between about 0° C. and 100° C.

7. The method of claim 6, wherein the temperature is about room temperature.

8. The method of claim 1, further comprising the steps of:
   waiting for the formation of an organic layer from the dilute aqueous suspension; and
   recovering the organic layer.

9. The method of claim 8, wherein the duration of the waiting is less than one minute.

10. The method of claim 8, wherein the organic layer is recovered by decanting the organic layer from the dilute aqueous suspension.

11. The method of claim 8, wherein the organic layer is recovered by mechanical separation of the organic layer from the dilute aqueous suspension.

\* \* \* \* \*